US012788786B2

(12) United States Patent
Fang et al.

(10) Patent No.: US 12,788,786 B2
(45) Date of Patent: Nov. 10, 2026

(54) BIFIDOBACTERIUM BREVE FOR IMPROVING AGING-RELATED COGNITIVE DISORDER AND USE THEREOF

(71) Applicant: WECARE PROBIOTICS CO., LTD., Jiangsu (CN)

(72) Inventors: Shuguang Fang, Jiangsu (CN); Zhonghui Gai, Jiangsu (CN); Yawen Shao, Jiangsu (CN); Yao Dong, Jiangsu (CN)

(73) Assignee: WECARE PROBIOTICS CO., LTD., Suzhou (CN)

(*) Notice: Subject to any disclaimer, the term of this patent is extended or adjusted under 35 U.S.C. 154(b) by 0 days.

(21) Appl. No.: 18/833,541

(22) PCT Filed: Nov. 16, 2023

(86) PCT No.: PCT/CN2023/131908

§ 371 (c)(1),
(2) Date: Jul. 26, 2024

(87) PCT Pub. No.: WO2025/081564

PCT Pub. Date: Apr. 24, 2025

(65) Prior Publication Data

US 2026/0000718 A1 Jan. 1, 2026

(30) Foreign Application Priority Data

Oct. 16, 2023 (CN) ........................ 202311331298.X

(51) Int. Cl.
*A61K 35/745* (2015.01)
*A61K 35/742* (2015.01)
*A61P 25/28* (2006.01)

(52) U.S. Cl.
CPC .......... *A61K 35/745* (2013.01); *A61K 35/742* (2013.01); *A61P 25/28* (2018.01)

(58) Field of Classification Search
None
See application file for complete search history.

(56) References Cited

FOREIGN PATENT DOCUMENTS

| | | | | |
|---|---|---|---|---|
| AU | 2017275210 | A1 | | 12/2017 |
| CN | 110934921 | A | | 3/2020 |
| CN | 112972502 | A | | 6/2021 |
| CN | 113215034 | A | | 8/2021 |
| CN | 113215035 | A | | 8/2021 |
| CN | 110777098 | B | * | 6/2022 |
| CN | 116179414 | A | | 5/2023 |
| CN | 116322724 | A | | 6/2023 |
| CN | 116731891 | A | | 9/2023 |
| CN | 116751727 | A | | 9/2023 |
| JP | WO2017/209156 | A1 | * | 12/2017 |

OTHER PUBLICATIONS

Nat Institute on Aging (Year: 2025).*
English google translation of CN110777098B (p. 1-15; 2025).*
English translation WO2017 (Year: 2017).*
Asaoka, et al., "Effect of Probiotic Bifidobacterium breve in Improving Cognitive Function and Preventing Brain Atrophy in Older Patients with Suspected Mild Cognitive Impairment: Results of a 24-Week Randomized, Double-Blind, Placebo-Controlled Trial" Journal of Alzheimer's Disease (2022) 88:75-95.
PCT/CN2023/131908, International Search Report, Dec. 22, 2023.
Chinese Patent Application 202311331298.X, Office Action, Nov. 30, 2023.
Xiao, et al., "Probiotic Bifidobacterium breve in Improving Cognitive Functions of Older Adults with Suspected Mild Cognitive Impairment: A Randomized, Double-Blind, Placebo-Controlled Trial" J. Alzheimers Dis. (2020) 77(1):139-147.

* cited by examiner

*Primary Examiner* — Patricia Duffy
(74) *Attorney, Agent, or Firm* — Robert C. Netter, Jr.; Dann, Dorfman, Herrell & Skillman

(57) ABSTRACT

Provided is a *Bifidobacterium breve* for improving an aging-related cognitive disorder and use thereof. The *Bifidobacterium breve* for improving the aging-related cognitive disorder is named *Bifidobacterium breve* BBr16 strain with a deposit number CGMCC No. 24471. The strain can significantly improve the aging-related cognitive disorder and can be used for preparing a product with an efficacy of preventing, improving or treating the aging-related cognitive disorder.

5 Claims, 7 Drawing Sheets

Specification includes a Sequence Listing.

BIFIDOBACTERIUM BREVE FOR IMPROVING AGING-RELATED COGNITIVE DISORDER AND USE THEREOF

This application is a § 371 application of PCT/CN2023/131908, filed Nov. 16, 2023, which claims priority to Chinese Patent Application No. 202311331298.X, filed on Oct. 16, 2023. The foregoing applications are incorporated by reference herein.

Incorporated herein by reference in its entirety is the Sequence Listing being concurrently submitted as a XML file named SeqList, created Jul. 25, 2024, and having a size of 3,193 bytes.

TECHNICAL FIELD

The present application belongs to the technical field of probiotic agents, relates to a *Bifidobacterium breve* BBr16 for improving an aging-related cognitive disorder and use thereof and, in particular, relates to a *Bifidobacterium breve* BBr16 strain, a culture including the *Bifidobacterium breve* BBr16 strain, a probiotic agent including the *Bifidobacterium breve* BBr16 strain and use of the *Bifidobacterium breve* BBr16 strain in preparation of a drug or a health care product for preventing, improving or treating an aging-related cognitive disorder.

BACKGROUND

As a trend of aging of a global population aggravates, an incidence of brain dysfunction including a neurodegenerative disease quickly increases. Although studies have proved some methods for alleviating these symptoms, memory deficit is still a serious problem in the old. As a main nutrient absorption organ, an intestinal tract contains about 1014 types of microorganisms. Intestinal floras maintain a balance under a normal physiological condition. The pathogenesis of an aging-related cognitive disorder is closely related to gut-liver axis imbalance and enterogenic endotoxemia. In addition, a lipopolysaccharide derived from the intestinal tract can promote an inflammatory response.

*Bifidobacterium*, a probiotic widely existing in an intestinal tract of a human body, is regarded as an important component of an intestinal microecological balance. With good adhesion, *Bifidobacterium* can maintain a structure of an intestinal flora and effectively protect the integrity of the morphology of an intestinal mucosa and a metabolic function. *Bifidobacterium* plays an important role in preventing and treating intestinal flora imbalance with a main mechanism including regulating the balance of floras in a manner of steric hindrance. In addition, *Bifidobacterium* can also produce multiple bacteriostatic components such as an acidic substance, an antimicrobial peptide and a biological enzyme, thereby inhibiting the growth and activity of a pathogenic bacterium. As a probiotic with characteristics of safety, health and no side effects, a *Bifidobacterium* microecological preparation can be colonized in an animal in vivo and can exert multiple beneficial health effects. Therefore, the *Bifidobacterium* microecological preparation is widely used in the field of clinical supplements.

At present, there is still a lack of particular drugs for the aging-related cognitive disorder. According to the pathogenesis and clinical pathway of the aging-related cognitive disorder, an anti-inflammatory cytokine, an antioxidant and a method for regulating intestinal floras can be selected for treating the aging-related cognitive disorder. In this context, it is particularly important to develop more probiotic products to improve the aging-related cognitive disorder.

SUMMARY

The present application provides a *Bifidobacterium breve* BBr16 for improving an aging-related cognitive disorder and use thereof and, in particular, provides a *Bifidobacterium breve* BBr16 strain, a culture including the *Bifidobacterium breve* BBr16 strain, a probiotic agent including the *Bifidobacterium breve* BBr16 strain and use of the *Bifidobacterium breve* BBr16 strain in preparation of a drug or a health care product for preventing, improving or treating an aging-related cognitive disorder.

In a first aspect, the present application provides a *Bifidobacterium breve* for improving an aging-related cognitive disorder. The *Bifidobacterium breve* for improving the aging-related cognitive disorder is named *Bifidobacterium breve* BBr16 strain and deposited on Mar. 7, 2022, with a deposit number CGMCC No. 24471.

In the present application, a new *Bifidobacterium breve* that can prevent or treat the aging-related cognitive disorder is separated from feces of a healthy infant fed with breast milk in Bama Yao Autonomous County, Guangxi, and deposited. The *Bifidobacterium breve* is named as *Bifidobacterium breve* BBr16 strain. The strain can significantly improve the aging-related cognitive disorder, which is embodied in the following aspects: (1) significantly decreasing aging scores of SAMP mice (rapid aging mice); (2) significantly increasing movement distances of the SAMP mice in an open field and dwell time spent by the SAMP mice in a central area, and decreasing delay time for arriving at a platform in a maze test; (3) significantly increasing contents of dopamine and 5-hydroxytryptamine in *striata* and hippocampi of brains of the SAMP mice; (4) decreasing levels of inflammatory factors TNF-α and IL-6 in pro-inflammatory cells in sera of the SAMP mice, and increasing levels of inflammatory factors IL10 in anti-inflammatory cells in the sera of the SAMP mice; and (5) significantly improving activity of SOD enzymes in livers of the mice, increasing contents of GSH in the livers, increasing levels of CAT enzymes in the livers, and decreasing levels of MDA in the livers. Therefore, the *Bifidobacterium breve* BBr16 strain can be used for preparing a product with an efficacy of preventing, improving or treating the aging-related cognitive disorder. As a probiotic, the BBr16 strain is high in safety and not easy to develop drug resistance.

Screening steps of the *Bifidobacterium breve* BBr16 strain involved in the present application are described below:

(1) selecting a sample separated from feces of a healthy infant fed with breast milk in Bama Yao Autonomous County, Guangxi, performing 10-fold gradient dilution with normal saline having a mass concentration of 0.9% three times, and coating on a solid medium; after 48 h of culture at 37° C., picking multiple colonies with different morphology, streaking and purifying on a surface of an improved MRS solid medium, and picking single colonies, expanding culture in a liquid medium at 37° C., and depositing in glycerol having a mass concentration of 40%;

(2) subjecting the deposited multiple single colonies to a physiological characteristic test in vitro, and screening a single strain with more excellent gastric acid and bile salt resistance (artificial simulation), identifying and depositing.

In a second aspect, the present application provides a culture of a *Bifidobacterium breve* for improving an aging-related cognitive disorder, wherein a method for preparing the culture includes: inoculating the *Bifidobacterium breve* BBr16 strain according to the first aspect in a medium, and culturing at 30-40° C. (for example, 30° C., 32° C., 35° C., 36° C., 37° C. or 38° C.) for 12-30 h (for example, 12 h, 14 h, 18 h, 20 h, 21 h, 22 h, 23 h, 24 h or 30 h).

Other specific point values within the preceding numerical ranges may be selected, and details are not described here.

The medium may be an MRS medium, wherein a formula composition of the MRS medium exemplarily includes a peptone, a beef extract, glucose, sodium acetate, yeast powder, ammonium citrate dibasic, $K_2PO_4{\cdot}3H_2O$, $MgSO_4{\cdot}7H_2O$, $MnSO_4$, L-cysteine and polysorbate 80 (Tween 80).

In a third aspect, the present application provides a probiotic agent for preventing, improving or treating an aging-related cognitive disorder, wherein a strain in the probiotic agent includes the *Bifidobacterium breve* BBr16 strain according to the first aspect.

The *Bifidobacterium breve* BBr16 strain involved in the present application may be used in a related product alone, or may be used in a related product in combination with another strain.

Preferably, a viable bacteria count of the *Bifidobacterium breve* BBr16 strain in the probiotic agent is not less than $1\times10^8$ CFU/mL or $1\times10^8$ CFU/g, for example, $1\times10^8$ CFU/mL (CFU/g), $1\times10^9$ CFU/mL (CFU/g), $2\times10^9$ CFU/mL (CFU/g), $5\times10^9$ CFU/mL (CFU/g), $8\times10^9$ CFU/mL (CFU/g), $1\times10^{10}$ CFU/mL (CFU/g), $5\times10^{10}$ CFU/mL (CFU/g) or $1\times10^{11}$ CFU/mL (CFU/g).

Other specific point values within the numerical ranges may be selected, and details are not described here.

Preferably, a dosage form of the probiotic agent includes lyophilized powder, a capsule, a tablet or a granule.

Preferably, the probiotic agent further includes a protective agent and/or an auxiliary additive.

Preferably, the protective agent includes skim milk powder.

The auxiliary additive includes any one or a combination of at least two of an inulin, a fructooligosaccharide, a galactooligosaccharide, a manno-oligosaccharide, trehalose, a soybean oligosaccharide, a resistant dextrin, *spirulina*, polydextrose, α-lactoalbumin or lactoferrin.

Preferably, the strain in the probiotic agent further includes a *Lactobacillus paracasei* LC86 strain, wherein the *Lactobacillus paracasei* LC86 strain is deposited on Jul. 20, 2020, with a deposit number CGMCC No. 1.12731.

In the present application, it is creatively found that the preceding BBr16 strain can be used in combination with the LC86 strain for preventing, improving or treating the aging-related cognitive disorder, which has a significantly excellent effect compared with a single bacterial agent or another combination manner, indicating that the BBr16 strain and the LC86 strain have a synergistic effect on the preceding efficacy.

Further preferably, a ratio of the viable bacteria count of the *Bifidobacterium breve* BBr16 strain to the viable bacteria count of the *Lactobacillus paracasei* LC86 strain is (3-5): 1, for example, 3:1, 7:2, 4:1, 9:2 or 5:1. Other specific point values within the numerical range may be selected, and details are not described here.

Based on a potential interaction between the BBr16 strain and the LC86 strain in the preceding efficacy, the two strains have a more excellent synergistic effect when satisfying the preceding particular mass ratio relationship.

In a fourth aspect, the present application provides use of the *Bifidobacterium breve* BBr16 strain according to the first aspect, the culture according to the second aspect or the probiotic agent according to the third aspect in preparation of a drug or a health care product for preventing, improving or treating an aging-related cognitive disorder.

Compared with the prior art, the present application has the beneficial effects below.

In the present application, the new *Bifidobacterium breve* that can prevent or treat the aging-related cognitive disorder is separated from the feces of the healthy infant fed with the breast milk in Bama Yao Autonomous County, Guangxi, and deposited, and named as *Bifidobacterium breve* BBr16 strain. The strain can significantly improve the aging-related cognitive disorder, which is embodied in the following aspects: (1) significantly decreasing the aging scores of the SAMP mice (the rapid aging mice); (2) significantly increasing the movement distances of the SAMP mice in the open field and the dwell time spent by the SAMP mice in the central area, and decreasing the delay time for arriving at the platform in the maze test; (3) significantly increasing the contents of dopamine and 5-hydroxytryptamine in the striata and hippocampi of the brains of the SAMP mice; (4) decreasing the levels of the inflammatory factors TNF-α and IL-6 in the pro-inflammatory cells in the sera of the SAMP mice, and increasing the levels of the inflammatory factors IL10 in the anti-inflammatory cells in the sera of the SAMP mice; and (5) significantly improving the activity of the SOD enzymes in the livers of the mice, increasing the contents of GSH in the livers, increasing the levels of the CAT enzymes in the livers, and decreasing the levels of MDA in the livers. Therefore, the *Bifidobacterium breve* BBr16 strain can be used for preparing the product with the efficacy of preventing, improving or treating the aging-related cognitive disorder. As the probiotic, the BBr16 strain is high in safety and not easy to develop the drug resistance.

DETAILED DESCRIPTION

Figure 1:
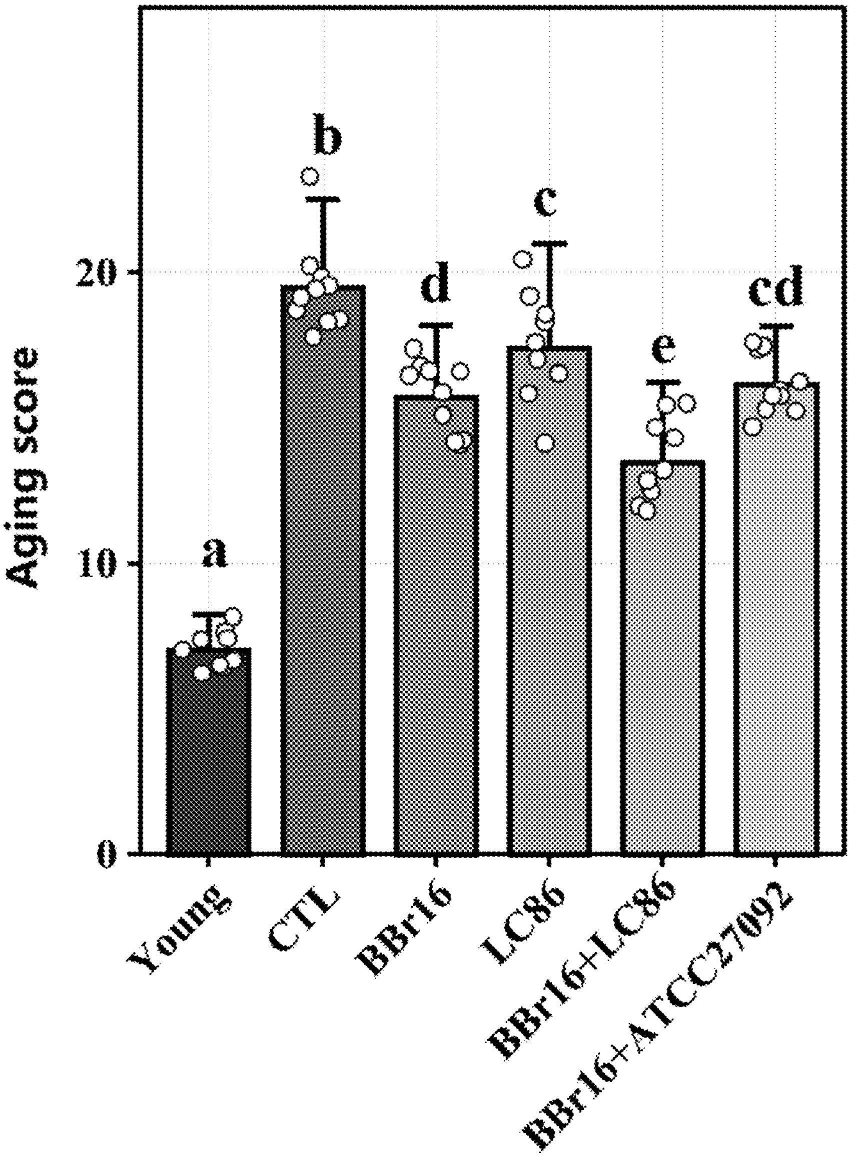
FIG. 1 is a statistical graph illustrating an evaluation result of an aging degree of each group of mice.

Technical solutions of the present application are further described below through specific examples. Those skilled in the art are to understand that the examples described herein are used for a better understanding of the present application and are not to be construed as specific limitations to the present application.

The *Bifidobacterium breve* BBr16 strain involved below is deposited in the China General Microbial Culture Collection Center on Mar. 7, 2022, with a deposit number CGMCC No. 24471, where the China General Microbial Culture Collection Center is located at No. 3 NO. 1 West Beichen Road, Chaoyang District, Beijing, China, 100101.

The *Lactobacillus paracasei* LC86 strain involved below is deposited in the China General Microbial Culture Collection Center on Jul. 20, 2020, with a deposit number CGMCC No. 1.12731, where the China General Microbial Culture Collection Center is located at No. 3 NO. 1 West Beichen Road, Chaoyang District, Beijing, China, 100101.

MRS solid media used as follows: 10 g of peptone, 10 g of beef extract, 20 g of glucose, 2 g of sodium acetate, 5 g of yeast powder, 2 g of ammonium citrate dibasic, 2.6 g of $K_2PO_4 \cdot 3H_2O$, 0.1 g of $MgSO_4 \cdot 7H_2O$, 0.05 g of $MnSO_4$, 20 g of agar and 0.5 g of L-cysteine were weighed and dissolved in deionized water, 1 mL Tween 80 was added, a volume of the solution was precisely adjusted to 1 L, and after sterilization and cooling, the mixture was poured into a sterilized Petri dish for later use.

MRS liquid media used as follows: 10 g of peptone, 10 g of beef extract, 20 g of glucose, 2 g of sodium acetate, 5 g of yeast powder, 2 g of ammonium citrate dibasic, 2.6 g of $K_2PO_4 \cdot 3H_2O$, 0.1 g of $MgSO_4 \cdot 7H_2O$, 0.05 g of $MnSO_4$ and 0.5 g of L-cysteine were weighed and dissolved in deionized water, 1 mL Tween 80 was added, a volume of the solution was precisely adjusted to 1 L, and after sterilization and cooling, the mixture was for later use.

Method for preparing the bacterial suspension involved in the following: required strains were inoculated in an MRS liquid medium and cultured for 24 h at 37° C. for activation two consecutive times to obtain an activation solution, the activation solution was inoculated in an MRS liquid medium at an inoculation dose of 2% (v/v) and cultured for 24 h at 37° C. to obtain a bacterial solution, the bacterial solution was centrifuged at 8000 g for 10 min, and the strains were resuspended with PBS to obtain the bacterial suspension.

Test animals were SPF-grade male SAMP8 mice, and feed of the mice was purchased from Shanghai SLAC Laboratory Animal Co., Ltd. Levels of TNFα, IL1b, IL6 and MCP1 were measured by an ELISA kit purchased from Shanghai Enzyme-linked Biotechnology Co., Ltd, and levels of superoxide dismutase (SOD), glutathione (GSH), peroxidase (CAT) and malondialdehyde (MDA) were measured by an assay kit purchased from Nanjing Jiancheng Bioengineering Institute.

A statistical method for the following graphs illustrating test results is as follows: using an R language (R4.2.2) for statistical analysis, and using a ggplot2 package for graphing. Different letters in a histogram indicate that there is a significant difference between groups ($p<0.05$).

Example 1

In this example, a *Bifidobacterium breve* for improving an aging-related cognitive disorder was screened out. Steps are described below.

(1) A sample separated from feces of a healthy infant fed with breast milk in Bama Yao Autonomous County, Guangxi, was selected, subjected to 10-fold gradient dilution with normal saline having a mass concentration of 0.9% three times and coated on a solid medium. After 48 h of culture at 37° C., multiple colonies that are different in morphology were picked and subjected to streaking purification on a surface of an improved MRS solid medium, and single colonies were picked, subjected to amplification culture in a liquid medium at 37° C. and deposited in glycerol having a mass concentration of 40%.

(2) The deposited multiple single colonies were subjected to a physiological characteristic test in vitro, and a single strain with more excellent gastric acid and bile salt resistance (artificial simulation) was screened out, which is specifically described below.

(2.1) Acid and Bile Salt Resistance Test

A pH of MRS media was adjusted to 3.0. After sterilization for 15 min at 121° C., liquid-cultured amplification cultures that had been activated for two generations were inoculated at an inoculation dose of 2% and cultured for 24 h at 37° C. Variations in absorbance ($\Delta OD_{600}$ values) of the liquid-cultured amplification cultures during 24 h were measured. 0.3% bovine bile salt was added to MRS media. After sterilization for 15 min at 121° C., liquid cultures that had been activated for two generations were inoculated at an inoculation dose of 2% and cultured for 24 h at 37° C., and variations in absorbance ($\Delta OD_{600}$ values) of the liquid cultures during 24 h were measured. Finally, ten strains with two relatively large $\Delta OD_{600}$ values were selected for the next test.

Acid resistance test: on the basis of a PBS buffer with pH=6.80, the pH was adjusted to 3.0 by 37% hydrochloric acid, liquid cultures that had been activated for two generations were inoculated at an inoculation dose of 10% after sterilization for 15 min at 121° C. and cultured at 37° C., and samples were taken at 0 min, 30 min, 60 min, 90 min and 120 min, respectively, and the viable bacteria counts were measured.

Bile salt resistance test: liquid cultures obtained after the strains had been activated for two generations were inoculated in MRS media containing different concentrations of bile salt (the media contained 0.1%, 0.2%, 0.3%, 0.5% and 2% bile salt, respectively) at an inoculation dose of 2%, an MRS medium containing no bile salt was used as a control, samples were taken after culture for 24 h at a constant temperature of 37° C., the viable bacteria counts were measured, and combined with the results of the previous one test, an excellent strain with acid resistance and bile salt resistance was screened out.

(2.2) Acid Generation Test

The acid generation of the strains was determined through a titration method. The strains deposited in glycerol tubes were taken, activated, inoculated in MRS liquid media at an inoculation dose of 2% and cultured for 18 h at a constant temperature. 10 mL of fermentation broth of each strain was taken and added to 50 mL of sterile water. Two to three drops of 1 g/L of phenolphthalein were added dropwise as an indicator. A 0.1 mol/L of NaOH standard solution was used for titration. The case where the solution appeared pink and did not fade after 30 s was used as a titration end-point. Each sample was in parallel for three times. An uninoculated MRS liquid medium was used as a blank control. A calculation formula is as follows: total acidity/$(g \cdot L^{-1}) = (V1-V2) \cdot c \cdot 100 \cdot V0^{-1}$ (V1 is a volume of a NaOH solution consumed by the sample, mL; V2 is a volume of a NaOH solution consumed by the blank control, mL; V0 is a total volume of a diluent, mL; c is a concentration of standard NaOH, mol/L).

Based on the preceding screening tests, a strain with the largest yield of lactic acid and the strongest gastric acid and bile salt resistance was selected.

-continued

```
TCTTTGAGTTTTAGCCTTGCGGCCGTACTCCCCAGGCGGGATGCTTAAC

GCGTTAGCTCCGACACGGAACCCGTGGAACGGGCCCCACATCCAGCATC

CACCGTTTACGGCGTGGACTACCAGGGTATCTAATCCTGTTCGCTCCCC
```

Example 2

In this example, the strain screened in Example 1 was subjected to physiological and biochemical characteristic and 16S rRNA molecular biological identification. Steps are described below.

(1) Physiological and biochemical characteristics are shown in the following Table 1:

TABLE 1

| Test Project | Result | Test Project | Result | Test Project | Result |
|---|---|---|---|---|---|
| Gram stain | positive | catalase | − | oxidase | − |
| cell morphology | polymorphic rod-shaped | | | | |
| Acid Generation of Carbohydrates (API 50CH) | | | | | |
| glycerol | − | inositol | − | inulin | − |
| erythritol | − | mannitol | + | melezitose | − |
| D-arabinose | − | sorbitol | + | raffinose | + |
| L-arabinose | − | α-methyl-D-mannoside | − | starch | + |
| D-ribose | + | α-methyl-D-glucoside | + | glycogen | + |
| D-xylose | − | N-acetyl-glucosamine | − | xylitol | + |
| L-xylose | − | amygdalin | + | gentiobiose | + |
| adonitol | − | arbutin | − | D-turanose | + |
| β-methyl-D-xyloside | − | aesculin | + | D-lyxose | − |
| D-galactose | + | salicin | + | D-tagatose | − |
| D-glucose | + | cellobiose | + | D-fucose | − |
| D-fructose | + | maltose | + | L-fucose | − |
| D-mannose | + | lactose | + | D-arabitol | − |
| L-sorbose | − | melibiose | + | L-arabitol | − |
| L-rhamnose | − | sucrose | + | gluconate | − |
| galactitol | − | trehalose | − | 2-keto-gluconate | − |

(2) 16S rDNA molecular biological identification

The strain deposited at −80° C. was taken out, inoculated in a centrifuge tube containing 20 mL of MRS liquid medium according to a proportion of 2%, cultured for 24 h at 37° C., centrifuged and separated. The centrifugation was performed at 8000 rpm for 15 min. Supernatant was removed, and the strains were collected. A genome of the strain was extracted, a general primer for bacteria was added for PCR amplification, and an amplification product was sent to Sangon Biotech (Shanghai) Co., Ltd. for sequencing and identification. The strain was subjected to sequencing and analysis. A 16S rDNA sequence of the strain is shown in SEQ ID No: 1. The sequence obtained through the sequencing was subjected to nucleic acid sequence alignment in GeneBank. The result shows that the strain is *Bifidobacterium breve*.

```
SEQ ID No: 1:
GCAAGGGGTTAGGCCACCGGCTTCGGGTGCTGCCCACTTTCATGACTTG

ACGGGCGGTGTGTACAAGGCCCGGGAACGCATTCACCGCGACGTTGCTG

ATTCGCGATTACTAGCGACTCCGCCTTCACGCAGTCGAGTTGCAGACTG

CGATCCGAACTGAGACCGGTTTTCAGGGATCCGCTCCAGCTCGCACTGT

CGCATCCCGTTGTACCGGCCATTGTAGCATGCGTGAAGCCCTGGACGTA

AGGGGCATGATGATCTGACGTCATCCCCACCTTCCTCCGAGTTAACCCC

GGCGGTCCCCCGTGAGTTCCCGGCACAATCCGCTGGCAACACGGGGCGA

GGGTTGCGCTCGTTGCGGGACTTAACCCAACATCTCACGACACGAGCTG

ACGACGACCATGCACCACCTGTGAACCCGCCCCGAAGGGAAACCCCATC

TCTGGGATCGTCGGGAACATGTCAAGCCCAGGTAAGGTTCTTCGCGTTG

CATCGAATTAATCCGCATGCTCCGCCGCTTGTGCGGGCCCCCGTCAATT
```

-continued

```
ACGCTTTCGCTCCTCAGCGTCAGTAACGGCCCAGAGACCTGCCTTCGCC

ATTGGTGTTCTTCCCGATATCTACACATTCCACCGTTACACCGGGAATT

CCAGTCTCCCCTACCGCACTCAAGCCCGCCCGTACCCGGCGCGGATCCA

CCGTTAAGCGATGGACTTTCACACCGGACGCGACGAACCGCCTACGAGC

CCTTTACGCCCAATAATTCCGGATAACGCTTGCACCCTACGTATTACCG

CGGCTGCTGGCACGTAGTTAGCCGGTGCTTATTCGAAAGGTACACTCAA

CACAAAGTGCCTTGCTCCCTAACAAAAGAGGTTTACAACCCGAAGGCCT

CCATCCCTCACGCGGCGTCGCTGCATCAGGCTTGCGCCCATTGTGCAAT

ATTCCCCACTGCTGCCTCCCGTAGGAGTCTGGGCCGTATCTCAGTCCCA

ATGTGGCCGGTCGCCCTCTCAGGCCGGCTACCCGTCGAAGCCATGGTGG

GCCGTTACCCCGCCATCAAGCTGATAGGACGCGACCCCATCCCATGCCG

CAAAGGCTTTCCCAACACACCATGCGGTGTGATGGAGCATCCGGCATTA

CCACCCGTTTCCAGGAGCTATTCCGGTGCATGGGGCAGGTCGGTCACGC

ATTACTCACCCGTTCGCCACTCTCACCACCAAGCAAAGCCCGATGGATC

CCGTTCGACT.
```

Based on the results of the 16S rDNA molecular biological identification and the morphological identification in Example 2, it is confirmed that the strain belongs to *Bifidobacterium breve*, which is named *Bifidobacterium breve* BBr16 strain.

Example 3

In this example, culture conditions of the *Bifidobacterium breve* BBr16 strain were optimized. Steps are described below.

The *Bifidobacterium breve* BBr16 strain was inoculated in an MRS liquid medium and separately cultured for 48 h at different temperatures of 10-50° C., and in a culture process, $OD_{600}$ values of a culture solution were measured with a microplate reader at intervals. The results are shown in Table 2.

TABLE 2

| Culture Condition | 2 h | 4 h | 8 h | 12 h | 20 h | 24 h | 30 h | 40 h | 48 h |
|---|---|---|---|---|---|---|---|---|---|
| 10° C. | 0.504 | 0.512 | 0.539 | 0.541 | 0.5 | 0.539 | 0.539 | 0.538 | 0.539 |
| 20° C. | 0.523 | 0.549 | 0.553 | 0.561 | 0.595 | 0.595 | 0.594 | 0.595 | 0.594 |
| 30° C. | 0.611 | 0.685 | 0.875 | 1.164 | 1.635 | 1.964 | 2.165 | 2.178 | 2.175 |
| 35° C. | 0.62 | 0.796 | 1.325 | 4.106 | 5.683 | 6.046 | 6.011 | 6.125 | 6.221 |
| 40° C. | 0.623 | 0.644 | 1.345 | 4.486 | 5.375 | 5.968 | 6.125 | 6.135 | 6.133 |
| 45° C. | 0.54 | 0.556 | 0.964 | 1.635 | 1.931 | 2.053 | 2.145 | 2.143 | 2.145 |
| 50° C. | 0.556 | 0.563 | 0.573 | 0.603 | 0.721 | 1.395 | 1.394 | 1.41 | 1.396 |

The results show that the *Bifidobacterium breve* BBr16 strain grows optimally at 35-40° C. and can be in a growth stabilization period after 18-22 h of culture.

Example 4

In this example, the gastric acid and bile salt resistance of the *Bifidobacterium breve* BBr16 strain was verified. Steps are described below.

(1) Preparation of Artificial Gastric Juice and Bile Salt

The artificial gastric juice contained 0.20% NaCl and 0.30% pepsin in mass fraction, a pH was separately adjusted to 2.0, 2.5 and 3.0 by HCl, and the mixture was filtered and sterilized for later use.

10% bovine bile salt: 10.0 g of bovine bile salt (Ourchem, Sinopharm Chemical Reagent Co., Ltd, Shanghai, China) was weighed into 100 mL of sterile water, and the mixture was filtered by a 0.22 μm filter membrane and sterilized.

MRS medium containing 0.1% bile salt: the MRS medium (Beijing Solarbio Science & Technology Co., Ltd) was prepared according to a specification, and after high-pressure steam sterilization (121° C., 15 min), a proper amount of 10% bovine bile salt solution was added until a final concentration was 0.1%.

(2) Gastric Acid Resistance Test 1.0 mL bacterial suspension of the *Bifidobacterium breve* BBr16 (with a concentration of $1\times10^9$ CFU/mL, where the concentration of the bacterial solution was measured through a method in a national standard GB4789.35-2016 *National Food Safety Standard—Microbiological Examination of Food—Examination of Lactic Acid Bacteria*) was separately mixed with 9.0 mL artificial gastric juice with a pH of 2.0, 2.5 and 3.0 and subjected to anaerobic standing culture at 37° C., samples were taken at the beginning (0 h) and 3 h after treatment, respectively, the viable bacteria count was measured through a pouring culture method, and a survival rate of the viable bacteria was calculated. A formula is as follows:

$$\text{survival rate (\%)} = N1/N0\times 100\%,$$

in the formula, N1 is the viable bacteria count 3 h after the treatment of the artificial gastric juice, and N0 is the viable bacteria count at 0 h. The test results are shown in Table 3.

TABLE 3

| Resistance | Survival Rate (%) |
|---|---|
| artificial gastric juice 2.0 | 81.5% |
| artificial gastric juice 2.5 | 90.1% |
| artificial gastric juice 3.0 | 93.7% |

(3) Bile Salt Resistance Test 1.0 mL bacterial suspension of the *Bifidobacterium breve* BBr16 (with a concentration of $1\times10^9$ CFU/mL, where the concentration of the bacterial solution was measured through the method in the national standard GB4789.35-2016 *National Food Safety Standard—Microbiological Examination of Food—Examination of Lactic Acid Bacteria*) was mixed with 9.0 mL MRS medium containing 0.1% bovine bile salt and subjected to anaerobic standing culture at 37° C., samples were taken at the beginning (0 h) and 3 h after treatment, respectively, the number of viable bacteria was measured through the pouring culture method, and a survival rate of the viable bacteria was calculated. A formula is as follows:

$$\text{survival rate (\%)} = N1/N0\times 100\%,$$

in the formula, N1 is the viable bacteria count 3 h after the treatment of the bile salt, and NO is the viable bacteria count at 0 h. The test result is a survival rate of 32%.

As can be seen from the preceding result, the *Bifidobacterium breve* BBr16 in the present application has good gastric acid resistance and choline resistance. The good gastric acid and bile salt resistance creates conditions for the *Bifidobacterium breve* BBr16 to be colonized in a gastrointestinal tract, maintain the homeostasis of a mucosal barrier of the gastrointestinal tract and prepare a product for preventing, improving or treating the aging-related cognitive disorder.

Example 5

In this example, effects of the *Bifidobacterium breve* BBr16 strain on aging scores, cognitive abilities, neurotransmitters, pro-inflammatory cytokines in sera and contents of oxidative stress markers of mice suffering from aging-related cognitive disorders were explored.

(1) Animal grouping: 50 adult male SAMP8 mice (22±2 g) at 16 weeks of age were randomly divided into five groups (ten mice for each group): a model control group (a CTL group), a *Bifidobacterium breve* BBr16 intervention group (a BBr16 group), a *Lactobacillus paracasei LC*86 intervention group (a LC86 group), a composite bacteria including *Bifidobacterium breve* BBr16 and *Lactobacillus paracasei* LC86 intervention group (a BBr16+LC86 group with a ratio of the viable bacteria count of 4:1) and a composite bacteria including *Bifidobacterium breve* BBr16 and *Lactobacillus paracasei* ATCC27092 intervention group (a BBr16+ATCC27092 group with a ratio of the viable bacteria counts of 4:1). Moreover, ten adult male SAMP8 mice (22±2 g) at 16 weeks of age were used as a young control group (a Young group). None of the mice had a specific pathogen. The mice were raised in cages alone. The environment was clean and quiet, with a temperature of 23-25° C. and humidity of 50 to 70%. Each group of mice were free to obtain food and water in an experimental period.

(2) Intervention method: BBr16 gavage was administered to the BBr16 group according to $1\times10^9$ CFU/day/mouse, LC86 gavage was administered to the LC86 group according to $1\times10^9$ CFU/day/mouse, gavage was administered to the BBr16+LC86 group according to a total bacteria amount of BBr16 and LC86 of $1\times10^9$ CFU/day/mouse, and distilled water (10 mL/kg) gavage was administered to the Young group and the CTL group. A suspension of distilled water and a probiotic was orally taken once per day for 12 consecutive weeks.

(3) An aging degree of the preceding each group of mice was evaluated by a grading scoring system. Each category had five grades, which were denoted as 0, 1, 2, 3 and 4, respectively. The higher the score was, the more severe the aging was. Indicators used in the evaluation include aspects such as a reactive behavior, a passive behavior, glossiness, roughness, hair loss, a skin ulcer, a periocular lesion, lordosis and kyphosis. Scores of the aspects were added to obtain a score of each mouse. Scoring criteria of the aging of the mice are shown in Table 4.

TABLE 4

| Project | Definition | Grade 0 | Grade 1 | Grade 2 | Grade 3 | Grade 4 |
|---|---|---|---|---|---|---|
| | | | (1) Behavior | | | |
| 1. reactive behavior | the most intensive exploratory response observed within 30 s | natural behavior | A. abnormal gait with no reduction in agility and behavioral patterns B. fidgetiness | significant decrease in agility and behavioral patterns | does not move on its own initiative, but will move if urged | motionless |
| 2. passive behavior | escape response caused by pinching the skin of the neck or hanging the forelimbs | the trouble of the natural escape response | reduction of escape response | the escape response to squeezing is lost, and the righting response of manual turn-over is reserved | there is no escape responses and no righting responses when the skin of the neck is pinched, and there is an escape response during forelimb suspension | zero escape response |
| | | | (2) Appearance 1. skin and hair | | | |
| ① glossiness | brightness | natural gloss | decrease in glossiness | the gloss completely disappears | the gloss completely disappears, and the hair looks very dirty | the gloss completely disappears, and the hair appears very dirty |
| ② roughness | hair thickness of the head, neck and back is determined according to the number of tiny patches of hair that can be felt | not rough | the region of the roughness is less than one region of the head | the area of the roughness is less than twice the area of the head | the area of the roughness is less than three times the area of the head | the gloss completely disappears, and the hair appears very dirty |

TABLE 4-continued

| Project | Definition | Grade 0 | Grade 1 | Grade 2 | Grade 3 | Grade 4 |
|---|---|---|---|---|---|---|
| ③ hair loss | hair loss or thinning of the head, neck and back except changes caused by ulcers or periocular lesions | no hair loss or thinning | A. the region of the hair loss is less than one region of the head B. the area of the hair thinning is less than ½ of the area | A. the region of the hair loss is greater than one region of the head, and the area of the hair loss is less than ¼ of the total area B. the area of the hair thinning is greater than ½ of the total area | the area of the hair loss is greater than ¼ but less than ½ of the total area | the area of the hair loss is greater than ½ of the total area |
| ④ skin ulcer | ulcers or healed ulcers over the entire skin except changes related to periocular lesions | no ulcers | healed ulcers or ulcers with crusts | the ulcers have no tendency to heal, and the ulcerated region is less than one region of the head | the ulcers have no tendency to heal, the ulcerated site is greater than one site of the head, and the area of the ulcers is less than ¼ of the area of the entire skin | the ulcers have no tendency to heal, and the area of the ulcers is greater than ¼ of the area of the entire skin |
| 2. eyes | | | | | | |
| ① periocular lesion | catarrhal changes in periocular region or facial swelling | no changes | catarrhal changes only around the eyes or metacarpal swelling | catarrhal changes extending to the nose | changes in diarrhea extend further | |
| ② capacity of cornea | opaque changes in rough cornea on lower surface of eyes when looking directly | no opacity | opacity with visible iris | the iris is opaque and visible, and the retinal reflex is positive after transillumination inspection | the entire cornea is opaque | |
| ③ coronary sulcus ulcer | opaque changes in rough cornea on lower surface of eyes when looking directly | no ulcers | linear ulcer corresponding to the palpebral fissure | ulcers extend to most regions | ulcers over the entire cornea | |

TABLE 4-continued

| Project | Definition | Grade 0 | Grade 1 | Grade 2 | Grade 3 | Grade 4 |
|---|---|---|---|---|---|---|
| ④ cataract | opaque changes in lens, no retinal reflexes after transillumination inspection and impossible complete eyeballs due to Grade 3 corneal opacity or ulcers that are present at the same time | natural reflexes | reduced reflexes | no reflexes | | |
| 3. vertebral column | | | | | | |
| ① kyphotic deformity of vertebral column | examination is performed through inspection and palpation | natural front and back curvatures | when the back is subjected to digital pressure, the increased curvature disappears | in the case of the combination of artificial head and neck traction and digital pressure on the back, the increased curvature disappears | permanent curvature | |

The evaluation result of the aging degree of each group of mice is shown in FIG. 1 (presented as an average value). As can be seen from the figure, compared with young mice (Young), the aging score of the model control group (CTL) is significantly increased. Compared with the model control group (CTL), the scores obtained after the intervention of the strains are decreased to different degrees. The BBr16+LC86 group is decreased to the highest degree, which is higher than the BBr16 group and the LC86 group, indicating that the BBr16 strain and the LC86 strain have a synergistic effect on improving the aging degree of the SAMP8 mice.

(4) The cognitive abilities were evaluated. Spatial learning and memory abilities of the mice were evaluated through an open field test and a water maze test.

Figure 2:
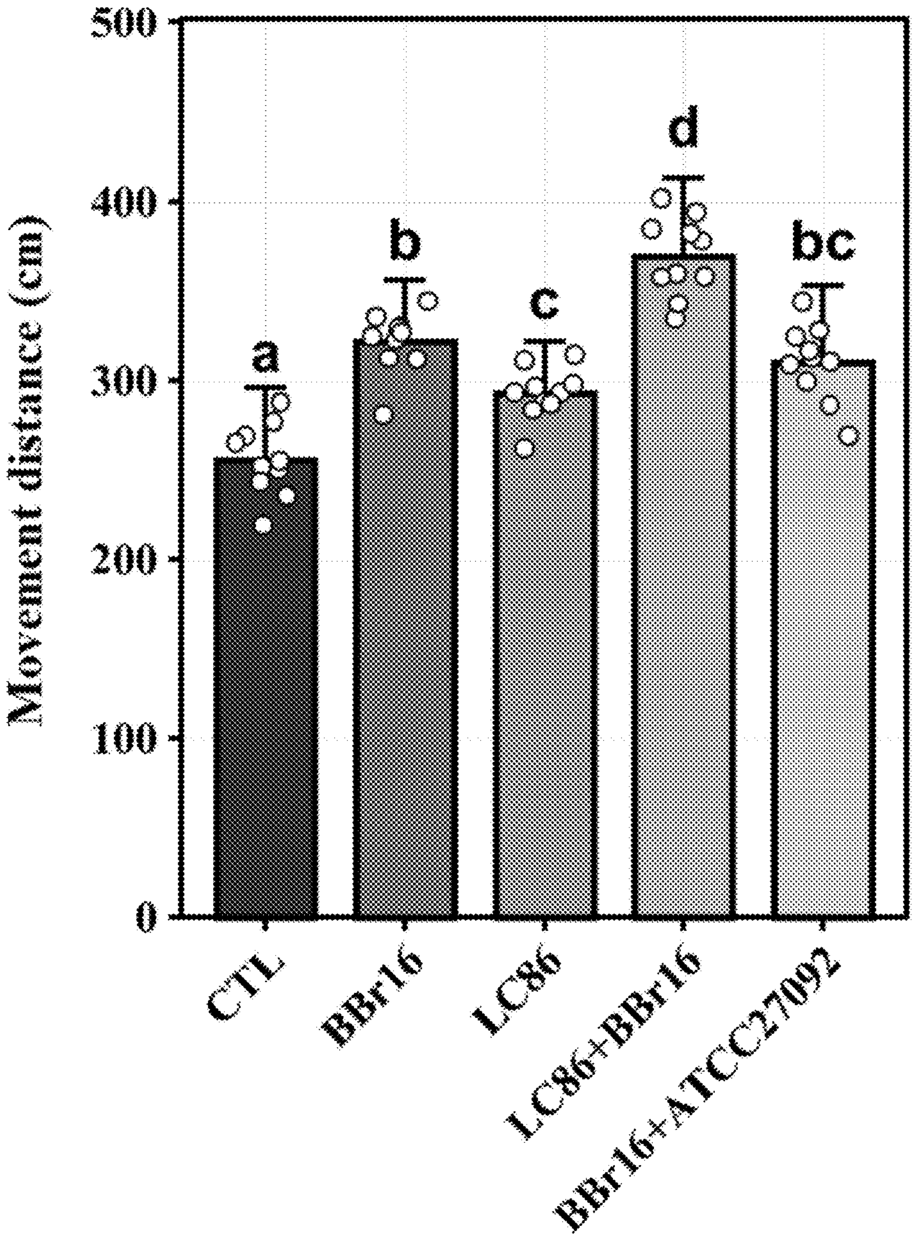
FIG. 2 illustrates a movement distance (cm) of each group of mice in an open field test.
Figure 3:
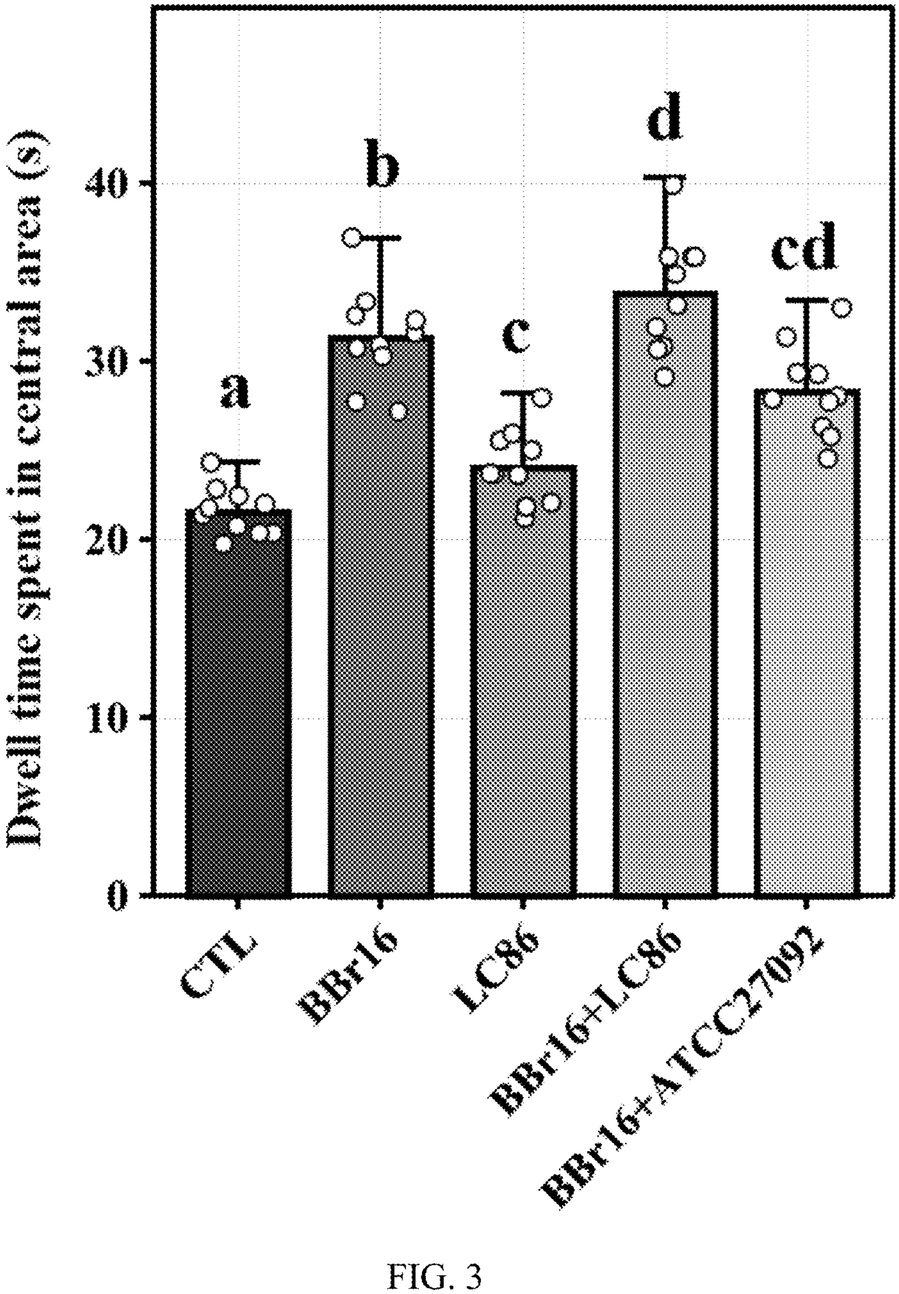
FIG. 3 illustrates dwell time(s) spent by each group of mice in a central area in an open field test.

Open field test method: the mice were gently transferred to an organic glass activity chamber with a size of 25×25×40 cm; the mice were allowed to explore the activity room freely for 10 min; behaviors of the mice in the open field activity chamber were observed and recorded, including movement distances (cm) and dwell time(s) spent in a central area; after each test, 70% ethanol was used for cleaning the chamber to reduce the interference of odors; the statistical results are shown in FIGS. 2 and 3 (presented as average values).

Figure 4:
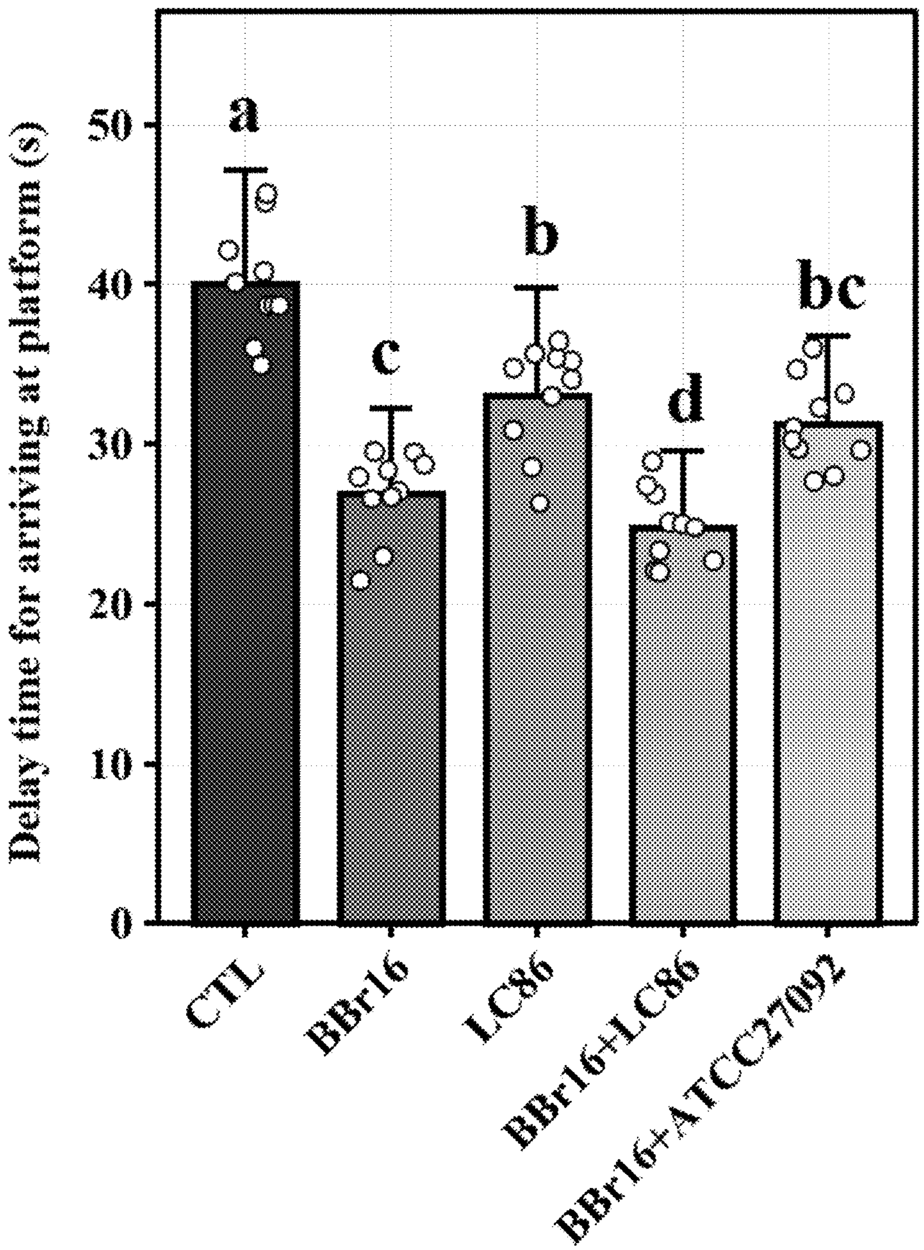
FIG. 4 illustrates delay time(s) for each group of mice to arrive at a platform in a water maze test.

Water maze test method: the test was carried out in a circular water pool with a diameter of 100 cm, a height of 40 cm, a water depth of 30 cm and a water temperature maintained at 26±1° C.; during six-day training, the mice were trained to find a platform underwater four times a day; if the mice cannot arrive at the platform within 60 s, the mice will be guided to the platform; on day 7, the platform was removed, and the mice were allowed 60 s to search a maze; swimming paths of the mice were analyzed by EthoVision video tracking software of Noldus; the delay time(s) for the mice to arrive at the platform was recorded; the statistical results are shown in FIG. 4 (presented as average values).

As can be seen from the results in the preceding figures, BBr16 can significantly improve the aging-caused cognitive disorders of the mice, and the BBr16+LC86 group has the best improvement ability, which is better than the BBr16 group and the LC86 group, indicating that the BBr16 strain and LC86 strain have a synergistic effect on improving the aging-caused cognitive disorders of the mice.

(5) Levels of the neurotransmitters in brains of the mice were affected. Levels of dopamine and 5-hydroxytryptamine in bilateral striata and hippocampi of each group of mice were investigated.

Figure 5:
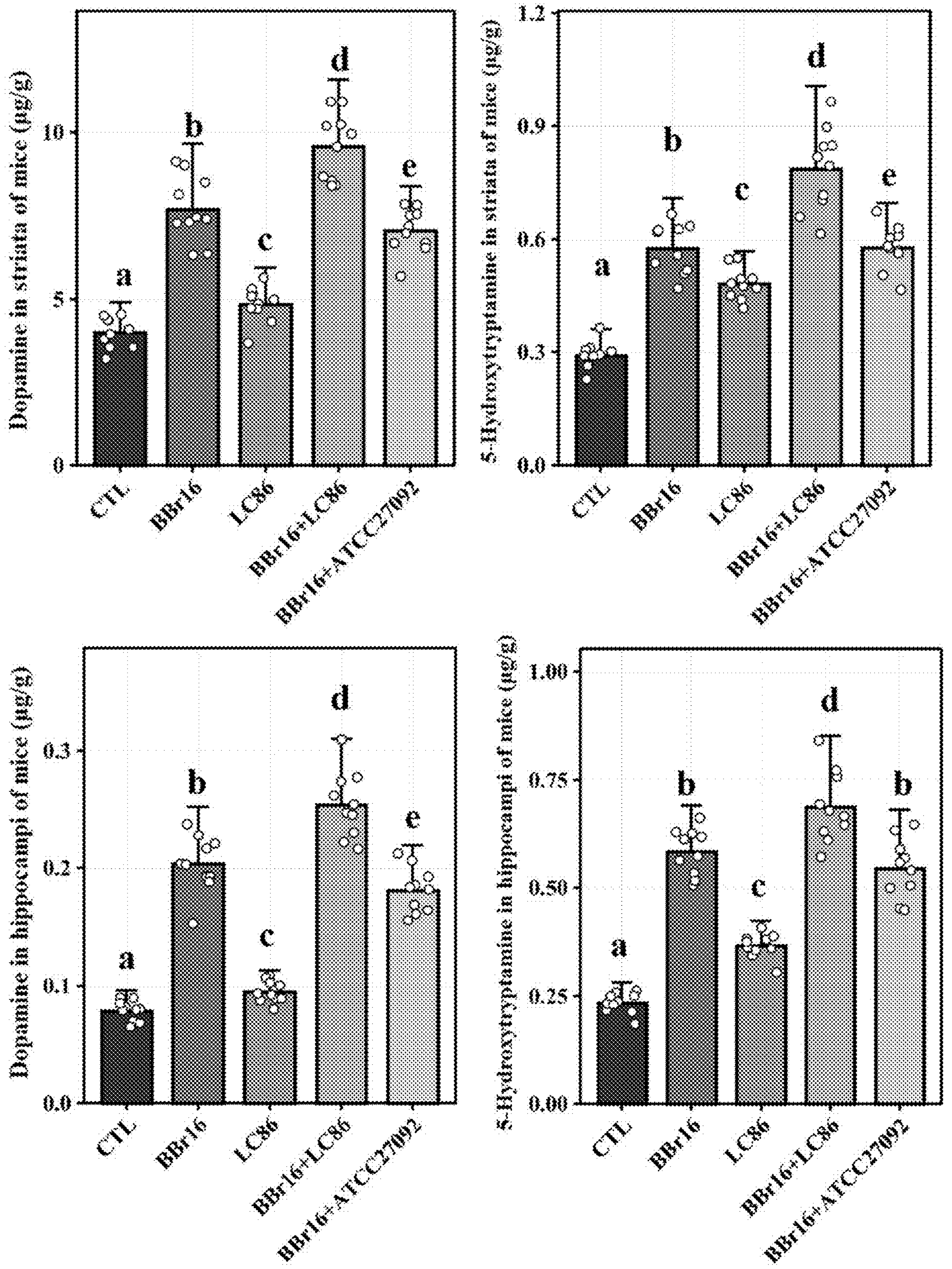
FIG. 5 is a statistical graph illustrating levels of dopamine and 5-hydroxytryptamine in bilateral striata and hippocampi of each group of mice.

Samples of the bilateral striata and hippocampi of the mice were acquired, homogenized and centrifuged at 12000 g for 10 min at 4° C. Supernatant was filtered by a 0.22 μm membrane, and filtered liquids were used for HPLC-MS detection. In HPLC, a Thermo Vanquish ultra-high performance liquid phase system of Thermo Fisher Scientific Inc. was used, and an ACQUITY UPLC HSS T3 column (2.1×150 mm, 1.8 μm) of Waters Corporation was used. A flow rate was set to 0.25 mL/min, a column temperature was set to 40° C., and an injection volume was set to 2 μL. In mass spectrometry, a Thermo Q Exactive Focus mass spectrometer detector of Thermo Fisher Scientific Inc. was used, and electrospray ionization (ESI) was separately used for data acquisition in positive ion and negative ion modes. The statistical results of each group are shown in FIG. 5 (presented as average values).

As can be seen from the results in the preceding figure, BBr16 can significantly improve the levels of dopamine and 5-hydroxytryptamine in the bilateral striata and hippocampi of the SAMP8 mice, and the BBr16+LC86 group is improved most significantly, which is superior to the BBr16 group and the LC86 group, indicating that the BBr16 strain has an excellent effect on improving the aging-related cognitive disorders and the BBr16 strain and the LC86 strain have a synergistic effect on the preceding efficacy.

(6) Levels of tumor necrosis factors TNFα, interleukin 6 (IL6), MCP1 and IL10 in sera of each group of mice were detected through an enzyme-linked immunosorbent assay (ELISA).

Figure 6:
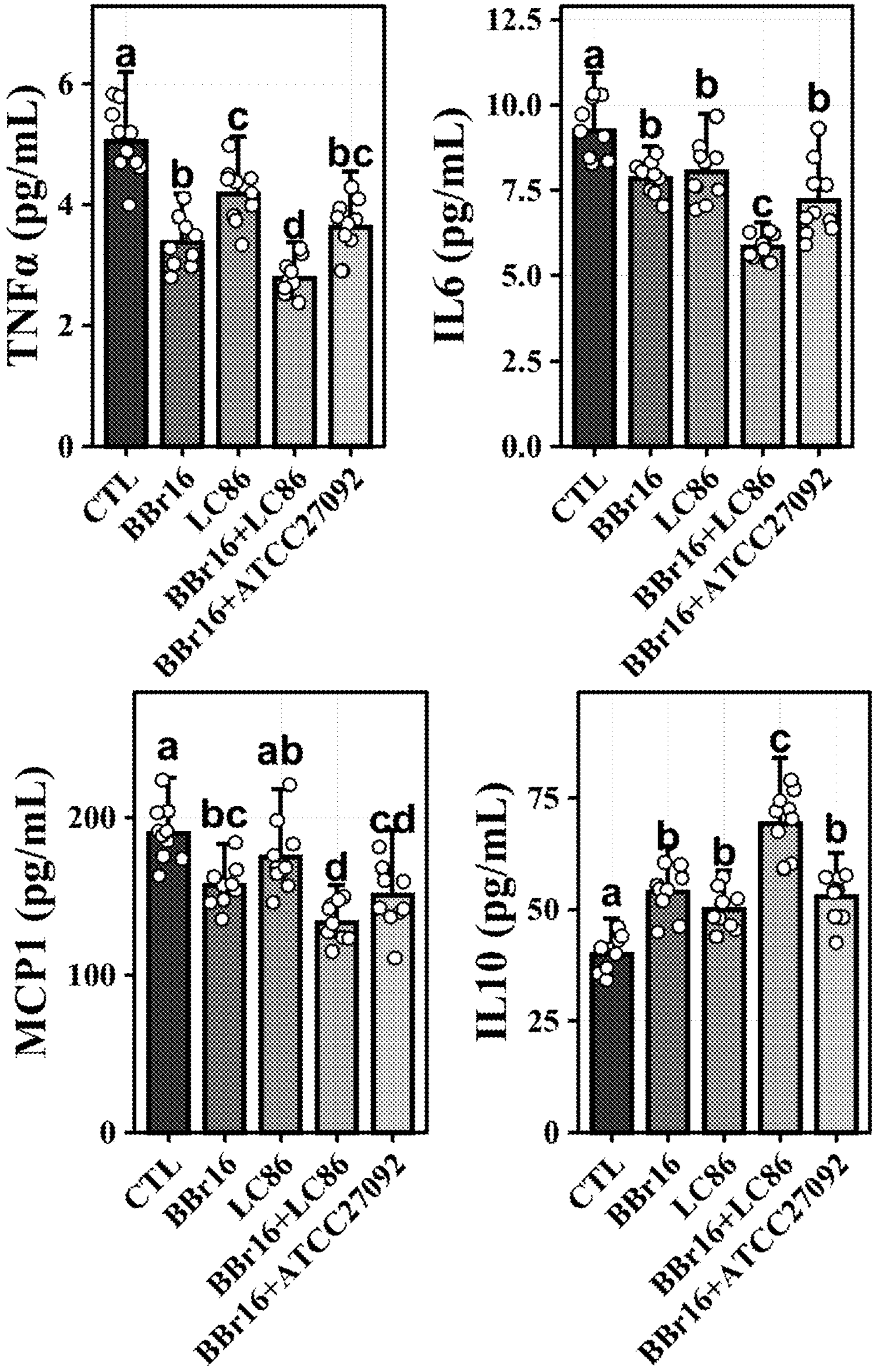
FIG. 6 is a statistical graph illustrating levels of tumor necrosis factors TNFα, interleukin 6 (IL6), MCP1 and IL10 in sera of each group of mice.

Serum samples of each group were acquired, and the levels of the tumor necrosis factors TNFα, interleukin 6 (IL6), MCP1 and IL10 in the sera were measured by the ELISA kit. The results are shown in FIG. 6. As can be seen from the results in the figure, after the BBr16 intervention is administered, the generation of TNFα, IL6 and MCP1 in the sera can be reduced, the generation of IL10 in the sera canbe promoted, and the effects of the BBr16+LC86 group are more apparent.

(7) Oxidative stress markers were detected.

After the assay, the mice were sacrificed, and colons of each group of mice were added to normal saline and homogenized to obtain 10% colon homogenates. The homogenates were centrifuged for 10 min (5,000 g, 4° C.) to obtain supernatant. Levels of superoxide dismutase (SOD), glutathione (GSH), peroxidase (CAT) and malondialdehyde (MDA) were measured by the assay kit of Nanjing Jiancheng Bioengineering Institute.

Figure 7:
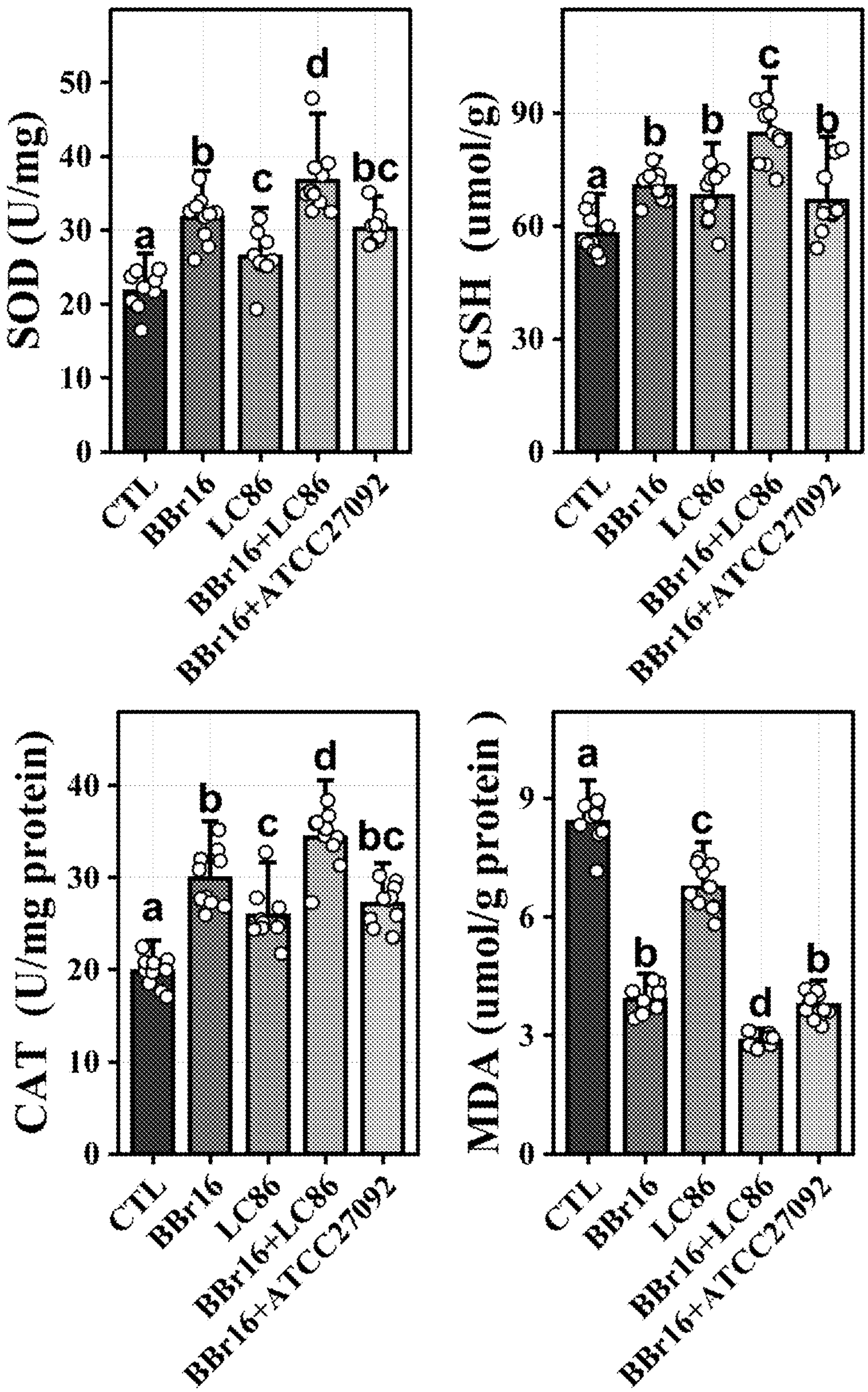
FIG. 7 is a statistical graph illustrating levels of superoxide dismutase (SOD), glutathione (GSH), peroxidase (CAT) and malondialdehyde (MDA) in colon tissues of each group of mice.

The results are shown in FIG. 7. As can be seen from the results in the figure, after the BBr16 intervention is administered, the levels of SOD, GSH and CAT can be improved, the levels of MDA can be reduced, and the effects of the BBr16+LC86 group are more apparent.

The applicant has stated that although the *Bifidobacterium breve* for improving the aging-related cognitive disorder and the use thereof in the present application are described through the preceding examples, the present application is not limited to the preceding examples, which means that the implementation of the present application does not necessarily depend on the preceding examples. It should be apparent to those skilled in the art that any improvements made to the present application, equivalent replacements of raw materials of the product of the present application, additions of adjuvant ingredients, selections of specific manners, etc., all fall within the protection scope and the disclosure scope of the present application.

In addition, it is to be noted that if not in collision, specific technical features described in the preceding specific examples may be combined in any suitable manner. To avoid unnecessary repetition, various possible combination manners are not further described in the present application.

What is claimed is:

1. A method for improving or treating an aging-related cognitive disorder, comprising administering an effective amount of *Bifidobacterium breve* BBr16 strain CGMCC No. 24471 and *Lactobacillus paracasei* LC86 strain CGMCC No. 1.12731 in a viable bacteria count ratio of 4:1.

2. The method of claim 1, wherein the *Bifidobacterium breve* BBr16 strain CGMCC No. 24471 and the *Lactobacillus paracasei* LC86 strain CGMCC No. 1.12731 are in a probiotic agent, and a viable bacteria count of the *Bifidobacterium breve* BBr16 strain in the probiotic agent is not less than $1\times10^8$ CFU/mL or $1\times10^8$ CFU/g.

3. The method of claim 2, wherein a dosage form of the probiotic agent comprises lyophilized powder, a capsule, a tablet or a granule.

4. The method of claim 2, wherein the probiotic agent further comprises a protective agent and/or an auxiliary additive.

5. The method of claim 4, wherein the protective agent comprises skim milk powder; and the auxiliary additive comprises any one or a combination of at least two of an inulin, a fructooligosaccharide, a galactooligosaccharide, a manno-oligosaccharide, trehalose, a soybean oligosaccharide, a resistant dextrin, *spirulina*, polydextrose, α-lactoalbumin or lactoferrin.

* * * * *

SEQUENCE LISTING

```
Sequence total quantity: 1
SEQ ID NO: 1          moltype = DNA  length = 1382
FEATURE               Location/Qualifiers
source                1..1382
                      mol_type = other DNA
                      organism = synthetic construct
SEQUENCE: 1
gcaaggggtt aggccaccgg cttcgggtgc tgcccacttt catgacttga cgggcggtgt  60
gtacaaggcc cgggaacgca ttcaccgcga cgttgctgat tcgcgattac tagcgactcc  120
gccttcacgc agtcgagttg cagactgcga tccgaactga gaccggtttt cagggatccg  180
ctccagctcg cactgtcgca tcccgttgta ccggccattg tagcatgcgt gaagccctgg  240
acgtaagggg catgatgatc tgacgtcatc cccaccttcc tccgagttaa ccccggcggt  300
cccccgtgag ttcccggcac aatccgctgg caacacgggg cgagggttgc gctcgttgcg  360
ggacttaacc caacatctca cgacacgagc tgacgacgac catgcaccac ctgtgaaccc  420
gccccgaagg gaaaccccat ctctgggatc gtcgggaaca tgtcaagccc aggtaaggtt  480
cttcgcgttg catcgaatta atccgcatgc tccgccgctt gtgcgggccc ccgtcaattt  540
ctttgagttt tagccttgcg gccgtactcc ccaggcggga tgcttaacgc gttagctccg  600
acacggaacc cgtggaacgg gccccacatc cagcatccac cgtttacggc gtggactacc  660
agggtatcta atcctgttcg ctccccacgc tttcgctcct cagcgtcagt aacggcccag  720
agacctgcct tcgccattgg tgttcttccc gatatctaca cattccaccg ttacaccggg  780
aattccagtc tcccctaccg cactcaagcc cgcccgtacc cggcgcggat ccaccgttaa  840
gcgatggact ttcacaccgg acgcgacgaa ccgcctacga gccctttacg cccaataatt  900
ccggataacg cttgcaccct acgtattacc gcggctgctg gcacgtagtt agccggtgct  960
tattcgaaag gtacactcaa cacaaagtgc cttgctccct aacaaaagag gtttacaacc  1020
cgaaggcctc catccctcac gcggcgtcgc tgcatcaggc ttgcgcccat tgtgcaatat  1080
tccccactgc tgcctcccgt aggagtctgg gccgtatctc agtcccaatg tggccggtcg  1140
ccctctcagg ccggctaccc gtcgaagcca tggtgggccg ttaccccgcc atcaagctga  1200
taggacgcga ccccatccca tgccgcaaag gctttcccaa cacaccatgc ggtgtgatgg  1260
agcatccggc attaccaccc gtttccagga gctattccgg tgcatggggc aggtcggtca  1320
cgcattactc acccgttcgc cactctcacc accaagcaaa gcccgatgga tcccgttcga  1380
ct                                                                 1382
```